United States Patent
Inbal et al.

(10) Patent No.: US 9,023,609 B2
(45) Date of Patent: May 5, 2015

(54) FGL-2 PROTHROMBINASE AS A DIAGNOSTIC TOOL FOR MALIGNANCY

(75) Inventors: Aida Inbal, Hod Hasharon (IL); Esther Rabizadeh, Be'er Yakov (IL)

(73) Assignees: Mor Research Applications Ltd., Tel Aviv (IL); Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 13/809,697

(22) PCT Filed: Jul. 11, 2011

(86) PCT No.: PCT/IL2011/000548
§ 371 (c)(1),
(2), (4) Date: Jan. 11, 2013

(87) PCT Pub. No.: WO2012/007940
PCT Pub. Date: Jan. 19, 2012

(65) Prior Publication Data
US 2013/0115645 A1    May 9, 2013

Related U.S. Application Data

(60) Provisional application No. 61/364,031, filed on Jul. 14, 2010.

(51) Int. Cl.
*C12Q 1/37*     (2006.01)
*G01N 33/574*   (2006.01)

(52) U.S. Cl.
CPC .............. *C12Q 1/37* (2013.01); *G01N 33/574* (2013.01)

(58) Field of Classification Search
None
See application file for complete search history.

(56) References Cited

U.S. PATENT DOCUMENTS

| | | |
|---|---|---|
| 6,403,089 B1 | 6/2002 | Levy et al. |
| 6,642,433 B1 | 11/2003 | Levy et al. |
| 2007/0128198 A1 | 6/2007 | Levy et al. |

FOREIGN PATENT DOCUMENTS

| | | | | |
|---|---|---|---|---|
| WO | 98/51335 A1 | 11/1998 | | |
| WO | 01/05948 A1 | 1/2001 | | |
| WO | WO 2007/133654 | * 11/2007 | ................ | B65B 1/04 |

OTHER PUBLICATIONS

Chaerkady et al., "A Quantitative Proteomic Approach for Identification of Potential Biomarkers in Hepatocellular Carcinoma", Journal of Proteome Research 2008, 7, 4289-4298.*

Su et al., "Fibrinogen-like protein 2/fibroleukin prothrombinase contributes to tumor hypercoagulability via IL-2 and IFN-γ", World J Gastroenterol, Oct. 21, 2008; 14(39): 5980-5989.*

Sharma et al., "Early detection of breast cancer based on gene-expression patterns in peripheral blood cells", Breast Cancer Research 2005, 7:R634-R644 (DOI 10.1186/bcr1203).*

Zhu et al., "Fibrinogen-like protein 2 fibroleukin expression and its correlation with disease progression in murine hepatitis virus type 3-induced fulminant hepatitis and in patients with severe viral hepatitis B", World J Gastroenterol 2005;11(44):6936-6940.*

DePrimo et al., "Expression profiling of blood samples from an SU5416 Phase III metastatic colorectal cancer clinical trial: a novel strategy for biomarker identification", BMC Cancer 2003, vol. 3.*

Raghothanna Chaerkady et al: "A Quantitative Proteomic Approach for identification of Potential Biomarkers in Hepatocellular Carcinoma", Journal of Proteome Research, vol. 7, No. 10, Oct. 3, 2008, pp. 4289-4298, XP55007768.

Ning Qin et al: "Role of Fibrogen-like Protein 2 Prothrombinase/Fibroleukin in Experimental and Human Allograft Rejection", Journal of Immunology, Jun. 1, 2005, vol. 174, No. 11, pp. 7403-7411, XP002659722.

Ghanekar Anand et al: "Endothelial induction of fgl2 Contributes to Thrombosis during acute vascular xenograft rejection", Journal of Immunology, May 1, 2004, vol. 172, No. 9, pp. 5693-5701, XP002659723.

Chan, CWY et al."Soluble Fibrogen-Like Protein 2/Fibroleukin Exhibits Immunosuppressive Properties: Supressing T Cell Proliferation and Inhibiting Maturation of Bone-Marrow Derived Dendritic Cells", (2003) Journal of Immunology, 170: pp. 4036-4044.

Levy, GA et al. "Molecular and Functional Analysis of the Human Prothrombinase Gene (HFGL2) and Its Role in Viral Hepatitis", (Apr. 2000) American Journal of Pathology, vol. 156, No. 4, pp. 1217-1225.

Yuwaraj, S. et al. "Genomic Characterization, Localization, and Functional Expression of FGL2, the Human Gene Encoding Fibroleukin: a Noval Human Procoagulant", (2001) Genomics 71: pp. 330-338.

Ding, JW et al. "Fulminant Hepatic Failure in Murine Hepatitis Virus Strain 3 Infection: Tissue-Specific Expression of a Novel fgl2 Prothrombinase", vol. 71, No. 12, (1997) Journal of Virology, pp. 9223-9230.

Kim, I. et al. "Molecular Cloning, Expression, and Characterization of Angiopoietin-related Protein", (1999) Journal of Biological Chemistry, vol. 274, No. 37, pp. 26523-26528.

Hancock, WW et al. "Intact type 7 immunity and immune-associated coagulative responses in mice lacking IFN-inducible fibrogen-like protein 2", (2004) PNAS USA, vol. 101, No. 9, pp. 3005-3010.

Su, K. et al. "Fibrogen-like protein 2/fibroleukin prothrombinase contributes to tumor hypercoagulability via IL-2 and IFN-", (2008) World J. Gastroenterol, 14(39): pp. 5980-5989.

* cited by examiner

*Primary Examiner* — Suzanne M Noakes
(74) *Attorney, Agent, or Firm* — Marsteller & Associates, P.C.

(57) ABSTRACT

The present invention reveals a strong correlation between FGL-2 prothrombinase activity levels and the presence of a malignant proliferative disorder in a subject. Thus, the present invention provides FGL-2 prothrombinase activity as a diagnostic tool for malignancy.

6 Claims, 3 Drawing Sheets

Fig. 3

FGL-2 PROTHROMBINASE AS A DIAGNOSTIC TOOL FOR MALIGNANCY

FIELD OF THE INVENTION

The present invention relates to the diagnosis of malignancy, and in particular to the use of FGL-2 prothrombinase activity as a diagnostic tool for its detection.

BACKGROUND OF THE INVENTION

All publications mentioned throughout this application are fully incorporated herein by reference, including all references cited therein.

Fibrinogen-like protein 2 (FGL-2)/fibroleukin, also known as FGL-2 prothrombinase has been cloned and identified, and shown to belong to the fibrinogen family of proteins [Ning Q, et al. (2005), *J Immunol,* 174: 7403-7411]. At the genetic level, mouse FGL-2 (mFGL-2) and human FGL-2 (hFGL-2) have been localized to chromosomes 5 and 7 respectively [Ning et al. (2005) id ibid]. The human gene is approximately 7 kb in length with 2 exons. From the nucleotide sequence of the human gene a 439 amino acid long protein is predicted. The gene encoding FGL-2 was originally cloned from cytotoxic T lymphocytes (CTL) and the encoded protein of 70 KDa shares a 36% homology to the fibrinogen β and γ chains and a 40% homology to the FRED (fibrinogen-related domain) of tenascin [Chan. C W Y et. al. (2003) *J Immunol,* 170: 4036-4044]. The murine and human proteins share 78% overall identity with greater conservation at the C terminus [Levy, G A et al. (2000) *Am J Pathol.* 156: 1217-1225; Yuwaraj, S. et al. (2001) *Genomics* 71: 330-338].

FGL-2 prothrombinase is a transmembrane protein which was shown to have a serine protease activity capable of directly cleaving prothrombin to thrombin in the absence of factor VII or factor X leading to fibrin deposition, thus triggering thrombosis [Ning et al. (2005) Id ibid]. The coagulation activity of FGL-2 was first described in a murine fulminant hepatitis model [Ding, J W et al. (1997) *J Virol,* 71: 9223-30]. FGL-2 prothrombinase is expressed by activated reticuloendothelial cells (macrophages and endothelial cells) as well by peripheral blood CD4+ and CD8+ T cells, which also secret it, however, the secreted protein is devoid of coagulation activity [Chan et al. (2003) id ibid]. Moreover, it was shown that distinct domains of FGL-2 are responsible for the prothrombinase and immunomodulatory activities of the molecule [Chan et al. (2003) id ibid]. Recombinant FGL-2 protein was previously shown to induce sprouting in vascular endothelial cells [Kim, I. et al. (1999) *J. Biol. Chem.,* 274, 26523-8]. When FGL-2 is expressed as a membrane-associated protein on activated macrophages and endothelial cells, it exhibits a coagulation activity capable of directly cleaving prothrombin to thrombin. FGL-2 accounts for the fibrin deposition and thrombosis associated with both experimental and human allograft rejection, which has been abrogated through the use of FGL-2 neutralizing antibodies or in FGL-2 knock out mice [Ghanekar, A. et al. (2004) J Immunol, 172, 5693-5701: Hancock, W W et. al. (2004) *PNAS USA,* 101, 3005-3010]. Macrophage induction of FGL-2 occurs through IFNγ, whereas FGL-2 transcription in endothelial cells occurs in response to TNFα, but not IFNγ [Hancock et al. (2004) id ibid]. Experimental data indicate that endothelial cells rather than leukocyte FGL-2 expression accounts for intravascular fibrin deposition [Ning et al. (2005) id ibid].

WO 98/51335 (and its corresponding US 2007/0128198, U.S. Pat. No. 6,642,433 and U.S. Pat. No. 6,403,089) describes the characterization, of the FGL-2 gene from human and mouse origin, as well as the use of antibodies against FGL-2 for the prevention of fibrin deposition associated with endotoxin shock, viral hepatitis, allograft and xenograft rejection, and fetal loss.

Su. K. et al. (2008) describe the expression of human FGL-2 protein and mRNA in tumor tissues [Su, K. et al. (2008) *World J. Gastroenterol.* 14(39): 5980-5989]. Interestingly, the authors observed that the normal tissue surrounding the tumor did not display overexpression of FGL-2, as observed in the tumor itself.

SUMMARY OF THE INVENTION

In the present invention, the inventors have unexpectedly found that FGL-2 prothrombinase activity is increased in tumor cell lines and in peripheral blood cells from patients with hematological and solid cancers.

Thus, the present invention relates to a method for the diagnosis or prognosis of a malignant proliferative disorder in a subject, through measuring FGL-2 prothrombinase activity, in a sample obtained from said subject. Essentially, detection of FGL-2 prothrombinase activity higher than control in a sample is indicative of the presence of a malignant disorder in said subject. Furthermore, when said activity remains high or increases over time in said subject, it is an indication of poor prognosis or resistance to therapy. In counterpart, decreasing FGL-2 prothrombinase activity over time indicates recovery for said subject.

Thus, the present invention presents a prothrombinase enzyme for use in the diagnosis or prognosis of malignant proliferative disorders.

In addition, the present invention provides a kit for diagnosis or prognosis of a malignant proliferative disorder, said kit comprising: (a) at least one reagent for measuring FGL-2 prothrombinase activity; (b) instructions for measuring FGL-2 prothrombinase activity in a sample; and optionally (c) at least one means for collecting a sample to be tested; and/or (d) at least one control sample.

BRIEF DESCRIPTION OF THE FIGURES

The photograph shows the 397 bp fragment of FGL-2 amplified by RT-PCR in PBMC sample.

Lane 1—1.00 bp DNA ladder marker from Promega.

Lane 2—The band represents a PCR-amplified 397 bp fragment of FGL-2 cDNA from PBMC.

The photograph shows the 397 bp fragment of FGL-2 amplified by RT-PCR in a HUVEC sample.

Lane 1—100 bp DNA ladder marker from Promega.

Lane 2—The band represents a PCR-amplified 397 bp fragment of FGL-2 cDNA from HUVEC.

The shift in fluorescent intensity represents FGL-2 expression, which is present only in TNFα-treated as opposed to non-treated HUVEC. FGL-2 was detected using anti-FGL-2 antibodies.

Abbreviations: Bl.=blank; Untr.=untreated; tr.=treated; fluor.=fluorescence; ce. co.=cell count.

DETAILED DESCRIPTION OF THE INVENTION

The present inventors have demonstrated that FGL-2 prothrombinase activity is significantly elevated in PBMC from cancer patients. This finding suggested that FGL-2 prothrombinase activity may be used as a diagnostic as well as a prognostic marker for cancer.

Thus, in a first, aspect, the present invention provides a method for the diagnosis of a malignant disorder in a subject, said method comprising the steps of: (a) measuring FGL-2 prothrombinase activity in a sample from said subject; and (b) comparing said FGL-2 prothrombinase activity with that of a control value; whereby a sample with FGL-2 prothrombinase activity higher than control is indicative of the presence of a malignant disorder in said subject.

In one particular example, the present invention provides a method for the diagnosis of a malignant disorder in a subject, wherein said method comprises measuring FGL-2 prothrombinase activity in a blood sample from a subject, or in peripheral blood mononuclear cells (PBMC), and comparing the activity measured in the sample from a subject with that of a control value; whereby a sample with FGL-2 prothrombinase activity higher than control is indicative of the presence of a malignant disorder in said subject.

In a second aspect, the present invention also provides a method for the prognosis of a malignant proliferative disorder in a subject, said method comprising the steps of: (a) measuring FGL-2 prothrombinase activity in a sample from said subject at different time points, said time points being before, during and after treatment of said disorder; and (b) comparing the values of FGL-2 prothrombinase activity obtained for the different time points defined in step (a); whereby increasing FGL-2 prothrombinase activity over time indicates a poor prognosis or resistance to therapy of said malignant proliferative disorder, whereas a decreasing FGL-2 prothrombinase activity over time indicates recovery or cure) of said subject.

In another aspect, the present invention provides a method for the diagnosis of malignancy in a sample, said method comprising the steps of: (a) measuring FGL-2 prothrombinase activity in a sample from a subject; and (b) comparing said FGL-2 prothrombinase activity with that of a control value; whereby a sample with FGL-2 prothrombinase activity higher than control is indicative of the presence of a malignant disorder in said sample.

In one embodiment of the methods of the invention, said sample is a blood sample and comprises FGL-2 expressing cells, in which FGL-2 prothrombinase activity can be measured. In particular, said blood sample comprises PBMC.

Any sample comprising mononuclear cells may be used in the methods described herein, including a cell culture-derived sample, e.g. cells from a culture of a blood sample.

As mentioned herein, prothrombinase activity is understood to be FGL-2 prothrombinase activity, since PBMC (including monocytes and lymphocytes) contain only FGL-2 and no other prothrombinase. Therefore addition of prothrombin (specific substrate) to the lysates of these cells containing FGL-2 (specific enzyme) is expected to generate thrombin (specific end product).

Measuring of FGL-2 prothrombinase activity is usually performed using the thrombin generation assay, as described herein in the Examples, and as previously described, for example, by Gbanekar and colleagues [Ghanekar et al. (2004) id ibid]. Essentially, cells obtained from a sample are placed in contact with prothrombin (obtained from a commercial source) in assay conditions suitable for FGL-2 prothrombinase activity. Assay conditions are known to the man skilled in the art and are exemplified in the Methods herein below. Thrombin generation may be detected through the cleavage of its chromogenic substrate, which results in changing the color, meaning that enzymatic activity of the generated thrombin is detected and measured through its end product. Nevertheless, other methods for detecting thrombin could be envisioned, including immunological methods, which could measure the a mount of thrombin gene rated directly, using e.g., anti-thrombin antibodies. As exemplified herein below, thrombin generation may be measured at regular intervals, at least once, at least twice, or at least three times preferably twice at 405 nm using an automated plate reader. Preferred time points are 0, 5 min, 10 min, 15 min, 20 min, 25 min, 30 min, 60 min, 90 min, 120 min, and 240 min. Thrombin activity in each sample is calculated based on a comparison with the standard curve generated by known concentrations of thrombin.

Thus, use of FGL-2 prothrombinase activity is herein contemplated for the detection and diagnosis of cancer per se, as well as in assessing prognosis of a cancer which has already been diagnosed. Alternatively, FGL-2 prothrombinase activity is also appropriate for cancer screening, since its detection is based on a blood sample, which is one of the most "patient-friendly" types of sample to be obtained from subjects.

The present invention may also be useful in monitoring the efficacy of cancer treatment. Monitoring the efficacy of treatment is essential for assessing prognosis of cancer treatment. Hence, the diagnostic method presented herein may be effected in a subject either before, during or after cancer treatment, and the analysis of the results obtained at each time point (the level of FGL-2 prothrombinase activity) compared to that in the normal population. When the pattern of FGL-2 prothrombinase activity of a subject is the closest to that of the normal population, it indicates a successful treatment, whereas a high or increasing level of FGL-2 prothrombinase activity may indicate poor prognosis, treatment, failure, and/or relapse, depending on each case.

Cancer treatment, as referred to herein, relates to any treatment for eradicating a proliferative, disease, including radiotherapy, chemotherapy, etc.

In a further aspect, the present invention provides a prothrombinase enzyme for use in the diagnosis (detection) or in evaluation of the prognosis of malignant disorders.

Specifically, said diagnosis or prognosis of malignant disorders is effected through the measurement of said prothrombinase enzyme activity in a sample. In general, finding: elevated prothrombinase enzyme activity when compared with that of a control value indicates the presence of a malignant disorder. In counterpart, a sample presenting a prothrombinase enzyme activity which is compatible, i.e., within, the range or lower than that of a control value, indicates the absence of a malignant disorder.

Prognosis of a malignant, disorder may be effected by measuring prothrombinase enzyme activity in a sample obtained on at least one time point throughout treatment. If a sample is obtained at only one time point, said time point, should be after treatment. An optimal procedure would involve measuring prothrombinase enzyme activity at least once before, during and after treatment of a malignant disorder. An elevation of said prothrombinase enzyme activity throughout time being indicative of no response to treatment or of poor prognosis, whereas a decrease of said prothrombinase enzyme activity throughout time being indicative of recovery or amelioration of the condition. Poor prognosis meaning that there is a worsening of the malignant disorder, which may, e.g. be demonstrated by the enlargement of a tumor, in case of solid tumors, or in an increase of circulating cancer cells, in case of leukemias.

As defined herein "sample" refers to any sample obtained from a subject, generally a mammalian subject, more specifically a human subject. Examples of biological samples include body fluids and tissue specimens. The source of the sample may be blood, cerebrospinal fluid, tissue scrapings, swabs taken from body regions (throat, vagina, ear, eye, skin, sores tissue, such as lymph nodes, or the like). Tissue specimens include tumor biopsies or biopsies from any organ, such as spleen, lymph nodes, liver, lung, mammary gland, pancreas, colon, uterus, skin, prostate, endocrine glands, esophagus, stomach, intestine, etc. In particular, a sample may be obtained from any lymphocyte-containing tissue.

In one particular embodiment, said sample comprises FGL-2 expressing cells, and/or said sample is a blood sample.

In another particular embodiment, said sample comprises peripheral blood mononuclear cells (PBMC).

As mentioned herein, said prothrombinase enzyme is FGL-2.

As used herein W describe the present invention, "tumor", "cancer", "malignant, proliferative disorder" and "malignancy" all relate equivalently to an uncontrolled hyperplasia of a tissue or organ. If the tissue is part of the lymphatic or immune systems, malignant cells may include, non-solid tumors of circulating cells. Malignancies of other tissues or organs may produce solid tumors.

When referring herein to the term malignant proliferative disorder, or cancer, it includes solid and non-solid tumors. More particularly, solid tumors include carcinomas, sarcomas, melanomas and adenomas. Some specific examples of cancer are pancreatic cancer, breast cancer, squamous cell carcinoma, multiple myeloma, prostate cancer, Langerhans' cell sarcoma, thyroid papillary cancer, melanoma, esophageal cancer, endometrial sarcoma, mammary gland cancer, mediastinal large cell lymphoma, Hodgkin lymphoma, lung carcinoma, small cell lung cancer or non-small-cell lung carcinoma, kidney, uterus, prostate, bladder, colon, or ovarian cancer.

Other solid tumors which may also be diagnosed by the diagnostic method of the invention are, for example, mixed tumors of salivary gland, tumors in lip and oral cavity, carcinoma of the eyelid and carcinoma of the conjunctiva, pharynx, larynx, paranasal sinuses, colonic adenomas, adenocarcinomas sarcomas, liposarcoma, myxoid, synovial sarcoma, rhabdomyosarcoma (alveolar), extraskeletal myxoid chondrosarcoma, Ewing's tumor, other include testicular and ovarian dysgerminoma, retinoblastoma. Wilms' tumor, neuroblastoma, malignant melanoma, mesothelioma, breast, skin, malignant melanoma of the conjunctiva, malignant melanoma of the uvea, retinoblastoma carcinoma of the lacrimal gland, sarcoma of the orbit, brain, spinal cord, vascular system, hemangiosarcoma, malignant lymphoma, such as Burkitt's or non-Hodgkin's and Kaposi's sarcoma.

Non-solid tumors that may be diagnosed by the method of the invention include, but are not limited to, myeloid leukemia such as chronic myelogenous leukemia, acute myelogenous leukemia, acute myelogenous leukemia with maturation, acute promyelocytic leukemia, acute non-lymphocytic leukemia, acute non-lymphocytic leukemia with increased basophiles, acute monocytic leukemia, acute myelomonocytic leukemia with eosinophilia, lymphocytic leukemia, such as acute lymphoblastic leukemia, chronic lymphocytic leukemia and myeloprobferative diseases.

The methods described herein for detection, diagnosis, assessment of prognosis, screening of cancer are suitable for any stage in cancer.

In that regard, it is important to be familiar with the systems of staging cancer. Staging is based on knowledge of the way cancer develops. Cancer cells divide and grow without control or order to form a tumor. As the tumor grows, it can invade nearby organs and tissues. Cancer cells can also break away from the tumor and enter the bloodstream or lymphatic system. By moving through the bloodstream or lymphatic system, cancer can spread from the primary site to form tumors in other organs, which are denominated metastasis.

Most types of cancer have TNM (Tumor size, Nodes invohement, Metastasis) designations, but some do not. For example, cancers of the brain and spinal cord are classified according to their cell type and grade. Different staging systems are also used for many cancers of the blood or bone marrow, such as lymphoma. The Ann Arbor staging classification is commonly used to stage lymphomas and has been adopted by both the AJCC (American Joint. Committee on Cancer) and the UICC (International Union Against Cancer). However, other cancers of the blood or bone marrow, including most types of leukemia, do not have a clear-cut staging system. Another staging system, developed by the International Federation of Gynecology and Obstetrics, is used to stage cancers of the cervix, uterus, ovary, vagina, and vulva. This system uses the TNM format. Additionally, childhood cancers are staged using either the TNM system or the staging criteria of the Children's Oncology Group, a group that conducts pediatric clinical trials.

The TNM staging system is as follows: T describes the si e of the tumor and whether it has invaded nearby tissue, N describes any lymph nodes that are involved, and M describes the presence of metastasis.

Primary Tumor (T)
TX Primary tumor cannot a evaluated
T0 No evidence of primary tumor
Tis Carcinoma in situ (early cancer that has not spread to neighboring tissue).
T1,T2,T3,T4 Size and/or extent of the primary tumor
Regional Lymph Nodes (N)
NX Regional lymph nodes cannot be evaluated.
N0 No regional lymph node involvement (no cancer found in lymph nodes)
N1,N2, Involvement of regional lymph nodes (number and/or extent of N3 spread)
Distant Metastasis (M)
MX Distant metastasis cannot be evaluated
M0 No distant metastasis (cancer has not spread to other parts of the body)
M1 Distant metastasis (cancer has spread to other parts of the body)

An example according to the TNM system would be: breast cancer T3 N2 M0, referring to a large tumor that has spread outside the breast to nearby lymph nodes, but not to other parts of the body. Prostate cancer T2 N0 M0 means that the tumor is located only in the prostate and has not spread to the lymph nodes or any other part of the body.

Many cancer registries, such as the NCI's Surveillance, Epidemiology, and End Results Program (SEER), use summary staging. This system is used for all types of cancer. It groups cancer cases into five main categories:

In situ is early cancer that is present only in the layer of cells in which it began;
Localized is cancer that is limited to be organ in which it began, without evidence of spread;
Regional is cancer that has spread beyond the original (primary) site to nearby lymph nodes or organs and tissues;
Distant is cancer that has spread from the primary site to distant organs or distant lymph nodes:
Unknown is used to describe cases for which there is not enough information to indicate a stage.

Another commonly used staging system uses roman numerals:

Stage 0: Carcinoma in situ (early cancer that is present only in the layer of cells in which it began).

Stage I, II and III: Higher numbers indicate more extensive disease, greater tumor size and/or spread of the cancer to nearby lymph nodes and/or organs adjacent to the primary tumor.

Stage IV: The cancer has spread to another organ.

In a further aspect the present invention provides a kit for diagnosis or prognosis of a malignant disorder, said kit comprising; (a) at least one reagent for measuring FGL-2 prothrombinase activity; and (b) instructions for measuring FGL-2 prothrombinase activity in a sample.

The kit of the invention may further comprise: (c) at least, one means for collecting a sample to be tested; and optionally (d) at least one control sample; wherein said (a) at least one reagent for measuring FGL-2 prothrombinase activity comprises its substrate prothrombin.

A non-limiting list, of reagents for measuring FGL-2 prothrombinase activity includes a prothrombinase substrate, prothrombin, buffers such as HEPES, Tris, or any other buffer suitable for prothrombinase reaction known in the art, any chromogenic substrate suitable for the determination of serine proteases, and any other necessary reagent known to the man skilled in the art.

A non-limiting list of means for collecting a sample to be tested includes syringes, needles, in particular blood collection needles, sample tubes, and any other device necessary for collecting as sample known to the man skilled in the art.

As referred to herein, the term "control" or "control sample" refer to a sample or pool of samples obtained from subjects not affected by proliferative malignant disorder, otherwise referred to as the "normal population". Similarly, "control value" relates to the level of thrombinase activity presented by a control sample. The "control value" may also refer to the mean value of thrombinase activity obtained from studies in the normal population. Thus, the "control sample" or "control value" is the source of reference with which to compare the sample that diagnose is sought after.

It is herein defined that said prothrombinase activity measured using the reagents provided b said kit represents FGL-2 prothrombinase activity.

In one embodiment, any such kit is a kit comprising reagents for measuring FGL-2 prothrombinase activity. The kit may further optionally comprise any other necessary reagents such as detectable moieties, enzyme substrates and color reagents. The particular reagents and other components included in the diagnostic kit of the present invention can be selected from those available, in the art in accord with the specific diagnostic method practiced in the kit. Such kit can be used to detect FGL-2 prothrombinase activity in biological samples, such as tissue samples, particularly whole blood, PBMC or other cells before and/or after culture, obtained from a subject.

The findings presented herein strongly suggest that the enhanced thrombin generation by mononuclear cells of cancer patients is the result of increased FGL-2 prothrombinase activity. One possible explanation to this phenomenon would be that malignant cells directly activate FGL-2 in monocytesilymphocytes. Thus, thrombin and pro-thrombinase activity, in particular FGL-2 prothrombinase activity, can be used as a marker of malignant process as well as a measure of disease extensiveness.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It: is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without, departing from the intended scope of the invention.

Unless defined otherwise, all technical and scientific terms used herein have the same meaning as commonly understood by one of ordinary skill in the art to which this invention is related.

EXAMPLES

Methods

General Methods of Molecular Biology

A number of methods of the molecular biology art are not detailed herein, as they are well known to the person of skill in the art. Such methods include PCR, expression of cDNAs, transfection of human cells, and the like. Textbooks describing such methods are, e.g., Sambrook et al, (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological techniques are not in each instance described herein in detail, like for example ELISA, Western Blot, as they are well known to the person of skill in the art. See, e.g., Harlow and Lane (1988) *Antibodies: a laboratory manual*, Cold Spring Harbour Laboratory.

Mononuclear Cells Isolation

Peripheral blood mononuclear cells (PBMC) were isolated from heparinized peripheral blood collected from normal controls and patients through centrifugation over Ficoll-Hypaque at 1,400 g at 22° C. for 12 mM.

Thrombin Generation Assay

The previously published assay with slight modification was used [Ghanekar et al. (2004) id ibid.]. A total of $1-5\times10^5$ of peripheral blood mononuclear cells (or any other cell type used in the assay) was mixed with equal volume of human prothrombin (Enzyme Research Laboratories) in reaction buffer (20 mM HEPES, 150 mM sodium chloride, 5 mM calcium chloride, pH 7.4) to give a final concentration of prothrombin of 10 µM. The reaction mixture was they incubated for 30 min at 37° C., followed by addition of 125 µl of cold assay buffer (50 mM Tris, 227 mM sodium chloride, 1% BSA and 1 sodium azide, pH 8.3) to each reaction. After centrifugation at 14,000 rpm for 5 minutes in order to pellet the cells, 145 μl of supernatant was transferred to a flat bottom 96-well plate. Fifteen μl of Chromozym T (Roche, catalog number 10 206 849 001), was added to each well and thrombin generation was measured. Chromozym TH™ (Tosyl-Gly-Pro-Arg-4-nitranilide acetate) is a chromogenic substrate used for the determination of serine proteases, especially thrombin, in aqueous solutions. Thrombin generation was measured at regular intervals (0, 5 min, 10 min, 15 min, 20 min, 25 min, 30 min, 60 min, 90 min, 120 min, and 240 min) at 405 nm using an automated plate reader. Thrombin activity in each sample was calculated based on a comparison with the standard curve generated by known concentrations of human thrombin (Sigma). The results were expressed either as maximal amplitude (MA) or thrombin generation rate (TGR). TGR was calculated as area under the curve (AUC) using the GraphPad Prism® statistical program. FGL-2 activity was therefore expressed as the amount of thrombin generated between two time points: 90 and 240 minutes.

Detection of FGL-2 mRNA, Expression in Normal PRMC and HUVEC Through RT-PCR

Figure 1:
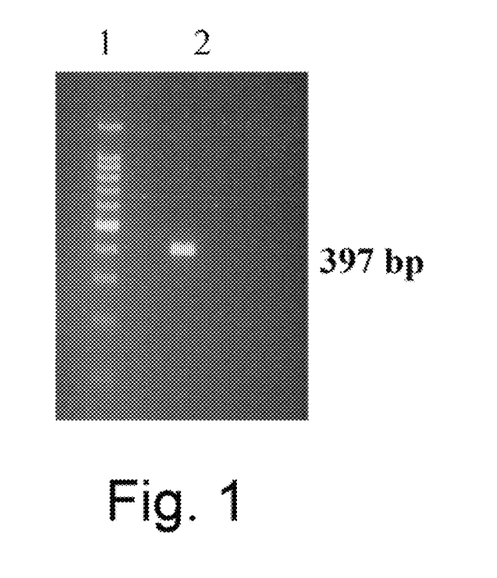
FIG. 1: FGL-2 mRNA expression in peripheral blood mononuclear cells (PRMC).
Figure 2:
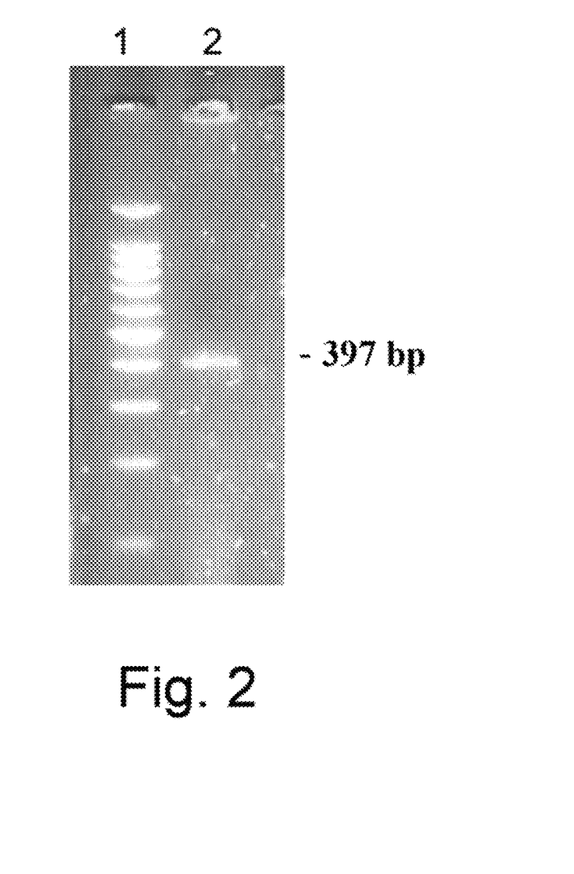
FIG. 2: FGL-2 mRNA expression in human umbilical vein endothelial cells (HUVEC).

PBMC and TNFα-stimulated HUVEC were obtained as detailed above. For PBMC, total RNA was extracted using the NucleoSpin® RNA II kit (Macherey-Nagel, Germany). For HUVEC, total cellular RNA was extracted using the TRI Reagent kit (Qiagen). Isolated RNA was then used as template in the RT-PCR reaction. FGL-2 cDNA was generated by RT-PCR using Titan One Tube RT-PCR Kit (Roche) and two nested oligonucleotides: forward 5'-acagaattcactgtaaagatgaagetggct-3 (SEQ. ID. NO. 1) and reverse 5'-tgtgaattettatggettaaagtgettggg-3' (SEQ. ID. NO. 2). The amplified 397 bp fragment of FGL-2 cDNA was analyzed by 2% agarose gel (FIGS. 1 and 2).

Flow Cytometry of HUVEC

Figure 3:
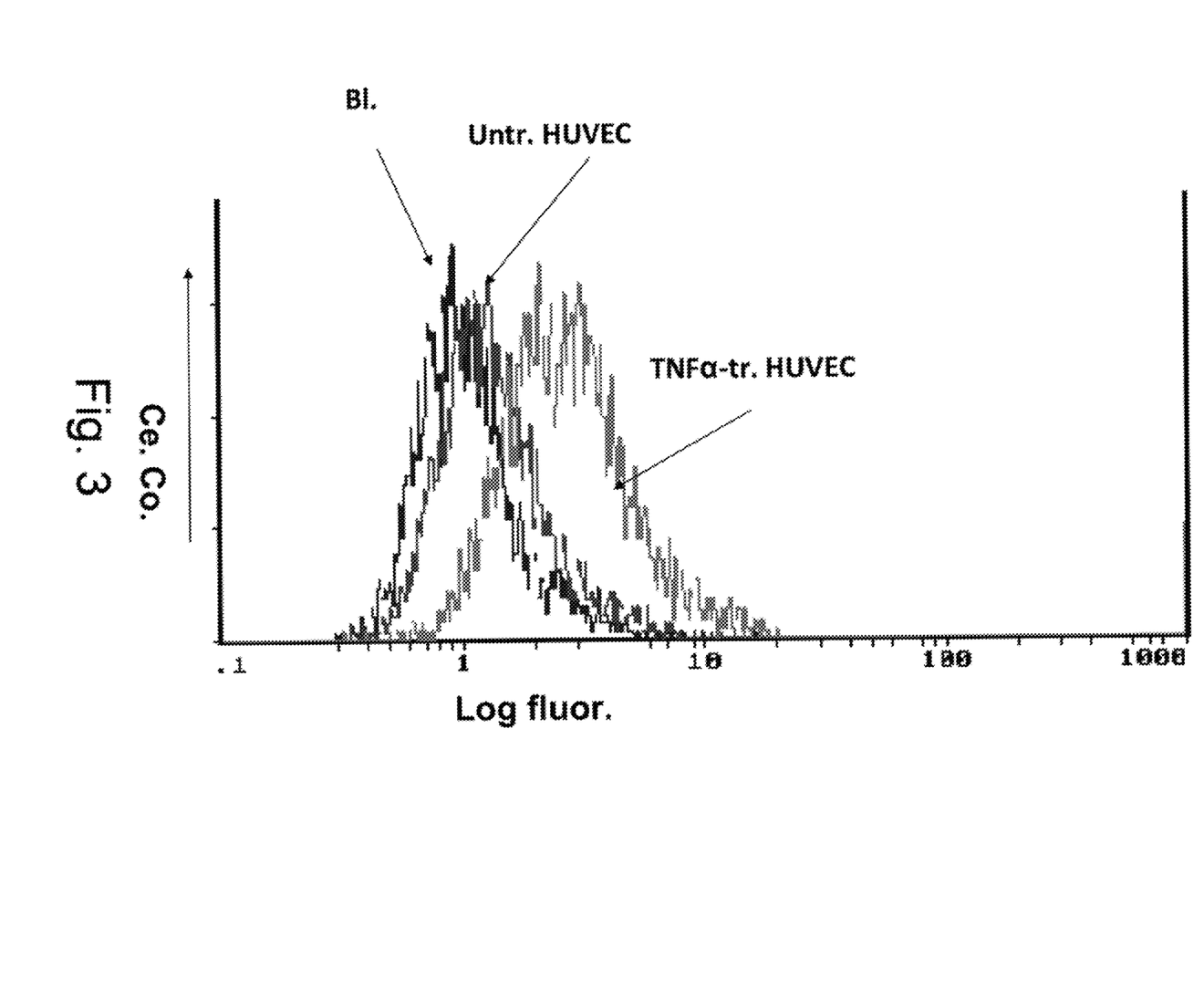
FIG. 3: Flow cytometry of FGL-2 protein expression in HUVEC.

Human umbilical vein endothelial cells (HUVEC), isolated from umbilical cord and cultured in the presence or absence of TNFα were incubated with anti-FGL-2 antibody (Santa Cruz, Calif.), followed b goat anti-rabbit-FITC. Labeled cells were detected by flow cytometry (Coulter), as shown in FIG. 3.

Example 1

FGL-2 prothrombinase activity was measured in peripheral blood mononuclear cells from normal controls (Table 1) and from patients with different types of cancer (Table 2) and compared. In addition, FGL-2 prothrombinase activity was measured in several cell lines (Table 3).

A significant increase in FGL-2 prothrombinase activity was observed in mononuclear blood cells from cancer patients. As compared to normal controls, FGL-2 prothrombinase activity of cancer samples at 90 and 240 minutes was 3.5 (p<0.04) and 4 (p<0.02) fold, respectively. In one patient (Table 2, Sample No. 10) FGL-2 prothrombinase activity decreased almost 5-fold following tumor burden reduction by chemotherapy (Table 2, Sample No. 15). In addition, increased FGL-2 prothrombinase activity was also observed in malignant, cell lines as compared to non-malignant cell cultures such as HUVEC, BHK and CHO cells (Table 3).

Interestingly, FGL-2 prothrombinase activity in HUVEC was only observed following maximal stimulation with TNFα (Table 3).

TABLE 1

FGL-2 prothrombinase activity in peripheral blood mononuclear cells from normal controls

| Sample No. | MA (ng/ml) 90 min | MA (ng/ml) 90 min average | MA (ng/ml) 240 min | MA (ng/ml) 240 min average |
|---|---|---|---|---|
| 1 | 759/480/558 824/573/641 | 639 | 1870/1250 | |
| 2 | 382 | 382 | | |
| 3 | 468 | 468 | | |
| 4 | 411 | 411 | | |
| 5 | 602/396 602/356 | 489 | 853/941 | 897 |
| 6 | 383 | 383 | 1231 | 1231 |
| 7 | 716 | 716 | 1648 | 1648 |
| 8 | 524/889 | 707 | 1206/1353 | 1280 |
| 9 | 954/602/ | 778 | 1577/1176 | 1367 |
| 10 | 1029/483/309 | 607 | 1083 | 1083 |
| 11 | 602/745/385/ 513/356 | 520 | 1041/1202 | 1122 |
| 12 | 757/568 | 663 | | |
| 13 | 658/877 | 768 | | |
| 14 | 988/741 | 865 | | |
| 15 | 645/860 | 753 | | |
| 16 | 761/1005 | 883 | | |
| 17 | 786/1050 | 918 | | |
| 18 | 705/940 | 823 | | |
| 19 | 678/904 | 791 | | |
| 20 | 658/877 | 768 | | |
| 21 | 908 | 908 | | |
| 22 | 645/855 | 750 | | |
| 23 | 743/990 | 867 | | |
| 24 | 614/818 | 716 | | |
| 25 | 614/873 | 744 | | |
| 26 | 734 | 734 | | |
| 27 | 774/483 | 629 | 1623/1250 | 1437 |
| 28 | 556/776 | 666 | 1264/1908 | 1586 |
| 29 | 716/882 | 799 | 1361/1648 | 1505 |
| 30 | 532 | 532 | 1135 | 1135 |
| 31 | 851 | 851 | 1406 | 1406 |
| 32 | 778 | 778 | 863 | 863 |
| Average | | 697 | | 1294 |
| SD | | 153 | | 250 |
| n | | 32 | | 14 |
| SE | | 27 | | 67 |

TABLE 2

FGL-2 prothrombinase activity in peripheral blood mononuclear cells from cancer patients

| Sample No. | Malignancy | Thrombin (ng/ml) 90 min | Average | Thrombin (ng/ml) 240 min | VTE |
|---|---|---|---|---|---|
| 1 | Pancreas Cancer Metastasis Stage 4 | 493.6/444 | 469 | 3544 | Yes |
| 2 | Pancreas Cancer | 915/930 | 923 | 7365 | Yes |
| 3 | Squamous Cell Carcinoma Stage 1 | 5041/1094 | 3068 | 9635 | Yes |
| 4 | Multiple Myeloma | 2176/1221 | 1699 | 9037 | No |
| 5 | Prostate Cancer Stage 2 | 688/819 | 754 | 6190 | No |
| 6 | Prostate Cancer | 1072/415 | | 3854 | No |
| 7 | Prostate Cancer Intermediate Risk | 680/1264 | 744 | 3418 | No |
| 8 | Pancreas Cancer | 741/1038 | 972 | 2727 | No |
| 9 | Breast Cancer Stage 2 | 996/1009 | | 4435 | No |
| 10 | Langerhans Cell Sarcoma | 1457/1375 | 890 | 16234 | No |
| 11 | Breast Ca | 3050/3434/ | 1003 | 3200 | No |
| 12 | Thyroid Papillary Ca | 1566 | 1416 | 2033 | No |
| 13 | Melanoma Stage 3 | 3649/2906 | 3242 | 2946 | No |
| 14 | Breast CA Stage 4 | 3046/2342 | 1566 | 3024 | No |

TABLE 2-continued

FGL-2 prothrombinase activity in peripheral blood mononuclear cells from cancer patients

| Sample No. | Malignancy | Thrombin (ng/ml) 90 min | Aver-age | Thrombin (ng/ml) 240 min | VTE |
|---|---|---|---|---|---|
| 15 | Following Treatment of Langerhans Cell Sarcoma | 3662/3209 | 3278 | 3441 | No |
| 16 | Multiple Myeloma | 5417 | 2694 | 5235 | No |
| 17 | Mediastinal Large Cell Lymphoma | 5201 | 3209 | 5089 | No |
| 18 | Hodgkin Lymphoma | 4754 | 5417 | 4817 | No |
| 19 | Pancreas Cancer | 4376 | 5201 | 4238 | No |
| 20 | Esophagus Ca | 3789/2903 | 4754 | 3879 | No |
| 21 | Endometrial Sarcoma | 3457 | 4376 | 3609 | Yes |
| Average | | | 2499 | 5140 | |
| SD | | | 1591 | 3229 | |
| n | | | 21 | 21 | |
| SE | | | 347 | 704 | |

VTE: Venous Thromboembolism

TABLE 3

FGL-2 prothrombinase activity in malignant cell lines and normal cell cultures

| Cell Line | Tumor/Cell Type | FGL-2 (ng/ml) 90 min |
|---|---|---|
| HL-60 | Promyelecytic Leukemia | 4090 |
| NB-4 p2 | APL | 3910 |
| U251 | Glioblastoma | 2660 |
| 22RV1 | Prostate Carcinoma | 2800 |
| JAR | Breast Carcinoma | 1467 |
| U87 | Neuroblastoma | 1650 |
| JURKAT P6 | Lymphoblastic Leukemia | 4070 |
| HT-20 p7 | Colon Adenocarcinoma | 3850 |
| DAUDI | Erythrocytic Leukemia | 2289 |
| | Non-Malignant Cell Cultures | |
| HUVEC | Human Umbilical Vein Endothelial Cells | 0 |
| HUVEC + TNFα | Human Umbilical Vein Endothelial Cells treated with TNFα | 1898 |
| CHO | Chinese Hamster Ovary | 0 |
| BHK | Baby Hamster Kidney | 0 |
| COS7 | Fibroblasts | 0 |

The invention claimed is:

1. A method for the diagnosis of a malignant proliferative disorder in a subject, said method comprising the steps of:
    (a) collecting a blood sample from said subject and a blood sample from a normal control;
    (b) isolating peripheral blood mononuclear cells (PBMC) from said samples;
    (c) measuring prothrombinase activity in the PBMC from said samples, using a thrombin generation assay, comprising generating thrombin from added prothrombin and determining the thrombin by using a chromogenic substrate; and;
    (d) comparing the prothrombinase activity of the PBMC from said subject with the prothrombinase activity from said control;
whereby a sample with prothrombinase activity higher than control is indicative of the presence of a malignant disorder in said subject.

2. The method of claim 1, wherein said malignant proliferative disorder is selected from the group consisting of pancreatic cancer, breast cancer, squamous cell carcinoma, multiple myeloma, prostate cancer, Langerhans' cell sarcoma, thyroid papillary cancer, melanoma, esophageal cancer, endometrial sarcoma, mammary gland cancer, mediastinal large cell lymphoma, Hodgkin lymphoma, lung carcinoma, small cell lung cancer or non-small-cell lung carcinoma, kidney cancer, uterus cancer, prostate cancer, bladder cancer, colon cancer, or ovarian cancer, mixed tumors of salivary gland, tumors in lip and oral cavity, carcinoma of the eyelid and carcinoma of the conjunctiva, Pharynx cancer, larynx cancer, paranasal sinuses cancer, colonic adenomas, adenocarcinomas, sarcomas, liposarcoma, myxoid or synovial sarcoma, rhabdomyosarcoma (alveolar), extraskeletal myxoid chondrosarcoma, Ewing's tumor, testicular or ovarian dysgerminoma, retinoblastoma, Wilms' tumor, neuroblastoma, malignant melanoma, mesothelioma, breast cancer, skin cancer, malignant melanoma of the conjunctiva, malignant melanoma of the uvea, retinoblastoma, carcinoma of the lacrimal gland, sarcoma of the orbit, brain cancer, spinal cord cancer, vascular system cancer, hemangiosarcoma, malignant lymphoma, Kaposi's sarcoma, myeloid leukemia, chronic myelogenous leukemia, acute myelogenous leukemia, acute myelogenous leukemia with maturation, acute promyelocytic leukemia, acute non-lymphocytic leukemia, acute non-lym-

SEQUENCE LISTING

<160> NUMBER OF SEQ ID NOS: 2

<210> SEQ ID NO 1
<211> LENGTH: 30
<212> TYPE: DNA
<213> ORGANISM: Homo sapiens

<400> SEQUENCE: 1
acagaattca ctgtaaagat gaagctggct                30

<210> SEQ ID NO 2
<211> LENGTH: 30
<212> TYPE: DNA
<213> ORGANISM: Homo sapiens

<400> SEQUENCE: 2
tgtgaattct tatggcttaa agtgcttggg                30 phocytic leukemia with increased basophiles, acute monocytic leukemia, acute myelomonocytic leukemia with eosinophilia, lymphocytic leukemia, acute lymphoblastic leukemia, chronic lymphocytic leukemia and myeloproliferative diseases.

3. The method of claim 1, wherein said PBMC are isolated through centrifugation from heparinized peripheral blood collected from said patient.

4. A method for the prognosis of a malignant proliferative disorder in a subject, said method comprising the steps of:
   (a) collecting blood samples from said subject at different time points and a blood sample from a normal control;
   (b) isolating peripheral blood mononuclear cells (PBMC) from said samples;
   (c) measuring prothrombinase activity in the PMBC from said samples, using a thrombin generation assay, comprising generating thrombin from added prothrombin and determining the thrombin by using a chromogenic substrate, said time points being before, during and after treatment of said disorder; and
   (d) comparing the values of prothrombinase activity obtained for the different time points in step (c);
   whereby increasing prothrombinase activity over time indicates a poor prognosis or resistance to therapy whereas a decreasing prothrombinase activity over time indicates recovery for said subject.

5. The method of claim 4, wherein said malignant proliferative disorder is selected from the group consisting, of pancreatic cancer, breast cancer, squamous cell carcinoma, multiple myeloma, prostate cancer, Langerhans' cell sarcoma, thyroid papillary cancer, melanoma, esophageal cancer, endometrial sarcoma, mammary gland cancer, mediastinal large cell lymphoma, Hodgkin lymphoma, lung carcinoma, small cell lung cancer or non-small-cell lung carcinoma, kidney cancer, uterus cancer, prostate cancer, bladder cancer, colon cancer, ovarian cancer, mixed tumors of salivary gland, tumors in lip and oral cavity, carcinoma of the eyelid and carcinoma of the conjunctiva, Pharynx cancer, larynx cancer, paranasal sinuses cancer, colonic, adenomas, adenocarcinomas, sarcomas, liposarcoma, myxoid or synovial sarcoma, rhabdomyosarcoma (alveolar), extraskeletal myxoid chondrosarcoma, Ewing's tumor, testicular or ovarian dysgerminoma, retinoblastoma, Wilms' tumor, neuroblastoma, malignant melanoma, mesothelioma, breast cancer, skin cancer, malignant melanoma of the conjunctiva, malignant melanoma of the uvea, retinoblastoma, carcinoma of the lacrimal gland, sarcoma of the orbit, brain cancer, spinal cord cancer, vascular system cancer, hemangiosarcoma, malignant lymphoma, Kaposi's sarcoma, myeloid leukemia, chronic myelogenous leukemia, acute myelogenous leukemia, acute myelogenous leukemia with maturation, acute promyelocytic leukemia, acute non-lymphocytic leukemia, acute non-lymphocytic leukemia with increased basophiles, acute monocytic leukemia, acute myelomonocytic leukemia with eosinophilia, lymphocytic leukemia, acute lymphoblastic leukemia, chronic, lymphocytic leukemia and myeloproliferative diseases.

6. The method of claim 4, wherein said PBMC are isolated through centrifugation from heparinized peripheral blood collected from said patient.

* * * * *